(12) United States Patent
Ichihara et al.

(10) Patent No.: US 9,233,031 B2
(45) Date of Patent: Jan. 12, 2016

(54) DISPOSABLE DIAPER

(75) Inventors: Keiko Ichihara, Kagawa (JP); Takuya Inoue, Kagawa (JP)

(73) Assignee: Unicharm Corporation, Ehime (JP)

( * ) Notice: Subject to any disclaimer, the term of this patent is extended or adjusted under 35 U.S.C. 154(b) by 233 days.

(21) Appl. No.: 13/985,837

(22) PCT Filed: Feb. 22, 2012

(86) PCT No.: PCT/JP2012/054322
§ 371 (c)(1),
(2), (4) Date: Aug. 15, 2013

(87) PCT Pub. No.: WO2012/117919
PCT Pub. Date: Sep. 7, 2012

(65) Prior Publication Data
US 2013/0331807 A1    Dec. 12, 2013

(30) Foreign Application Priority Data
Mar. 2, 2011 (JP) .................................. 2011-045725

(51) Int. Cl.
*A61F 13/49* (2006.01)
*A61F 13/496* (2006.01)
*A61F 13/514* (2006.01)

(52) U.S. Cl.
CPC ..... *A61F 13/49011* (2013.01); *A61F 13/51496* (2013.01)

(58) Field of Classification Search
CPC ...................... A61F 13/49011; A61F 13/51496
See application file for complete search history.

(56) References Cited

U.S. PATENT DOCUMENTS

| 2004/0133180 A1 | 7/2004 | Mori et al. | |
| 2008/0132871 A1* | 6/2008 | Otsubo | A61F 13/15593 604/385.23 |
| 2011/0077609 A1* | 3/2011 | Kuwano | A61F 13/49011 604/385.01 |
| 2013/0281954 A1* | 10/2013 | Ishihara et al. | 604/385.3 |

FOREIGN PATENT DOCUMENTS

| JP | 2002-272783 A | 9/2002 |
| JP | 2006-525858 A | 11/2006 |
| WO | WO 2009-119139 A1 | 10/2009 |
| WO | WO 2009/119195 A1 | 10/2009 |

OTHER PUBLICATIONS

International Search Report based on corresponding PCT application No. PCT/JP2012/054322 dated May 21, 2012 (3 pgs).

* cited by examiner

*Primary Examiner* — Susan Su
(74) *Attorney, Agent, or Firm* — Brinks Gilson & Lione

(57) ABSTRACT

A disposable diaper utilizing graphics to visually confirm whether the waist elastics are properly cut or cut off. A disposable diaper has a skin-facing side and a non-skin-facing side defining front and rear waist members, and includes an inner sheet lying on the skin-facing side, an outer sheet lying on the non-skin-facing side, waist elastics interposed between the inner and outer sheets and extending under a potential contractility in a transverse direction of the front and rear waist members, front and rear inelastic regions in which none of the waist elastics is present and graphic sheets having graphics adapted to be visually recognized through the outer sheet. End portions of the waist elastics interposed between the graphic sheets and the outer sheet extend from the outside of the graphic sheets across opposite side edges of the respective graphic sheets into the respective graphic sheets.

17 Claims, 7 Drawing Sheets

FIG.4
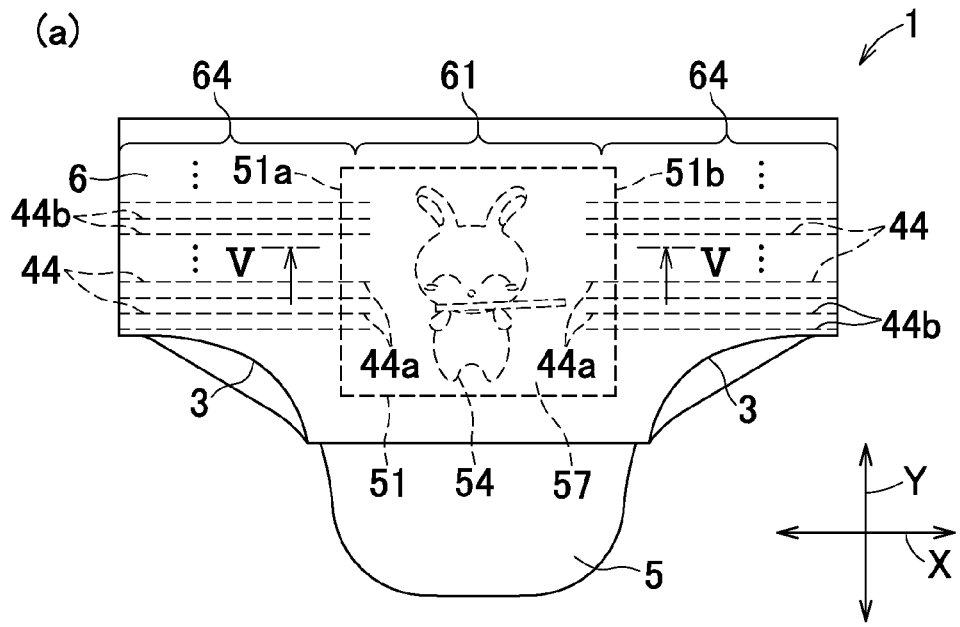
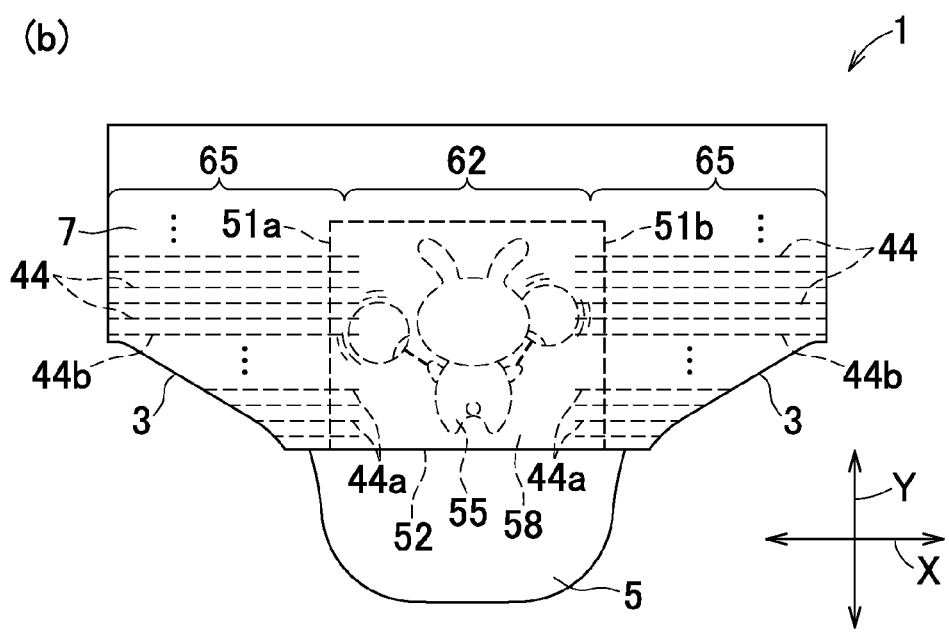

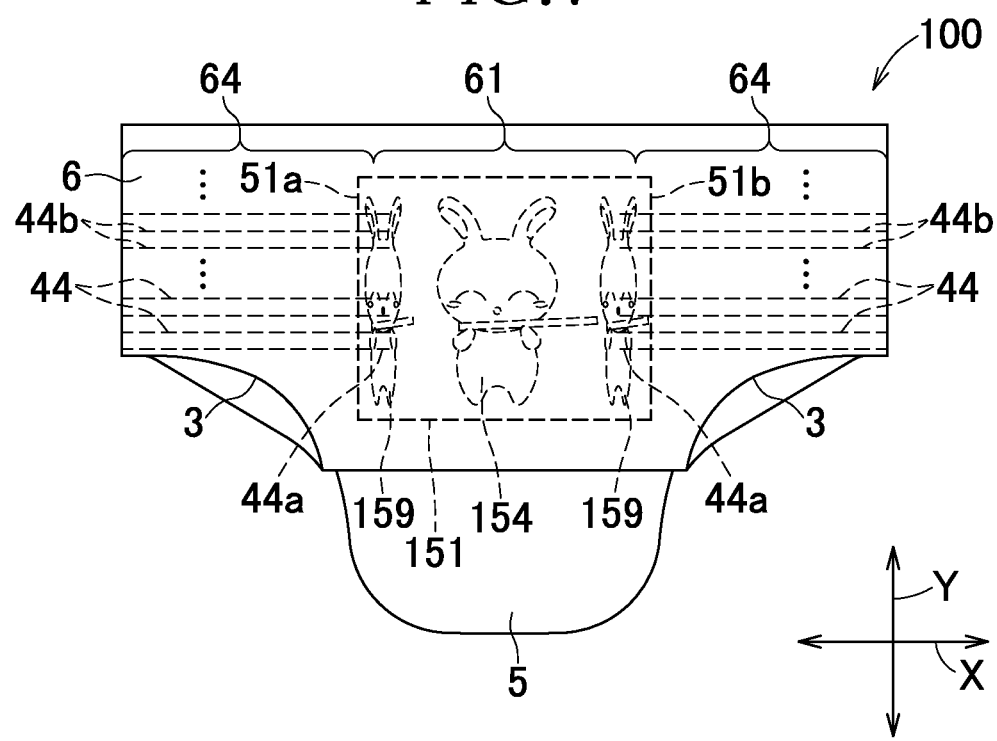

DISPOSABLE DIAPER

RELATED APPLICATION

This application is a 35 U.S.C. §371 national phase filing of International Patent Application No. PCT/JP2012/054322, filed Feb. 22, 2012, through which and to which priority is claimed under 35 U.S.C. §119 to Japanese Patent Application No. 2011-045725, filed Mar. 2, 2011.

TECHNICAL FIELD

This invention relates to disposable diapers and more particularly to disposable diapers such as toilet-training pants and incontinent briefs.

BACKGROUND

Conventionally, disposable diapers including front and rear waist members adapted to cover the wearer's waist are known. For example, JP 2006-525858 A (PTL 1) discloses front and rear waist members respectively having an inner sheet lying on the skin-facing side, an outer sheet lying on the non-skin-facing side and, between the inner sheet and the outer sheet, waist elastics and graphic sheets formed with the graphics.

The waist elastics are attached under tension in a body-cross direction between the inner and outer sheets.

In this disposable diaper, the waist elastics are cut off in the regions in which the graphic sheets are set so that no contractile force might be exerted on the graphic sheets. By cutting off the waist elastics, the graphic displaying regions are free from the contractile force of the waist elastics and, in consequence, the graphics should not get wrinkled and become less-visible.

CITATION LIST

Patent Literature

{PTL 1} JP 2006-525858 A

SUMMARY

Technical Problem

However, the invention disclosed in PTL 1 describes no technical idea utilizing the graphics to visually recognize whether operation of cutting back or cutting off the waist elastics is being properly carried out or not.

An object of the present invention is to provide a disposable diaper improved to be visually recognizable to the naked eyes whether the waist elastics are properly cut or cut off with the aid of the graphics.

Solution to Problem

The present invention provides a disposable diaper having a skin-facing side and a non-skin-facing side, including:

an inner sheet lying on the skin-facing side and an outer sheet lying on the non-skin-facing side each defining the front and rear waist members;

waist elastics interposed between the inner and outer sheets and extending under a potential contractility in a transverse direction of the front and rear waist members;

inelastic regions in which none of the waist elastics is present; and graphic sheets having graphics adapted to be visually recognized through the outer sheet.

In the disposable diaper, respective end portions of the waist elastics interposed between the graphic sheets and the outer sheet extend from the outside of the graphic sheets across opposite side edges of the respective graphic sheets into the respective graphic sheets.

According to one embodiment of this invention, the end portions of the waist elastics have no contractility and the remaining portions thereof have contractility; and the portions of the waist elastics having contractility extend from the outside of the respective graphic sheets across the opposite side edges thereof into the respective graphic sheets.

According to another embodiment of this invention, the end portions of the waist elastics lie on the respective graphics.

According to still another embodiment of this invention, the end portions of the waist elastics lie between the opposite side edges of the respective graphic sheets and the respective graphics.

According to further another embodiment of this invention, the respective graphic sheets include at least central graphics and lateral graphics arranged on both sides of the central graphics; and the end portions of the waist elastics lie between the opposite side edges of the respective graphic sheets and the respective central graphics.

According to yet another embodiment of this invention, the noncontractile end portions of the waist elastics lie on the respective lateral graphics.

According to an alternative embodiment of this invention, the respective graphics are different from the waist elastics in at least one of color phase, color saturation and brightness.

According to another alternative embodiment of this invention, the respective graphics are partially low in brightness and the waist elastics are relatively high in brightness.

According to still another alternative embodiment of this invention, the diaper further includes a liquid-absorbent structure; and a distribution direction of a first adhesive with which the inner sheet is joined to the respective graphic sheets intersects with a distribution direction of a second adhesive with which the inner sheet is joined to the liquid-absorbent structure.

According to further another alternative embodiment of this invention, the diaper further includes the liquid-absorbent structure containing therein a core material assembly; and, in the transverse direction, a width dimension of the core material assembly is substantially the same as a width dimension of each of the graphic sheets.

Advantageous Effects of Invention

In one or more embodiments of the disposable diaper according to this invention, the noncontractile end portions of the waist elastics are interposed between the respective graphic sheets and the outer sheet and extend from the outside of the respective graphic sheets across the opposite side edges thereof into the respective graphic sheets. With this arrangement, these end portions of the waist elastics may be visually recognized from the non-skin-facing side of the outer sheet and the graphics may be utilized to recognize easily with the naked eyes whether the operation of cutting or cutting off of the waist elastics is properly going on.

BRIEF DESCRIPTION OF DRAWINGS

FIG. 4(*a*) is a front view of the diaper and FIG. 4(*b*) is a rear view of the diaper.

FIG. 7 is a front view illustrating a substantial part of the disposable diaper according to a second embodiment.

DESCRIPTION OF EMBODIMENTS

Embodiments of a disposable diaper according to this invention will be described hereunder with reference to the accompanying drawings.

First Embodiment

Figure 1:
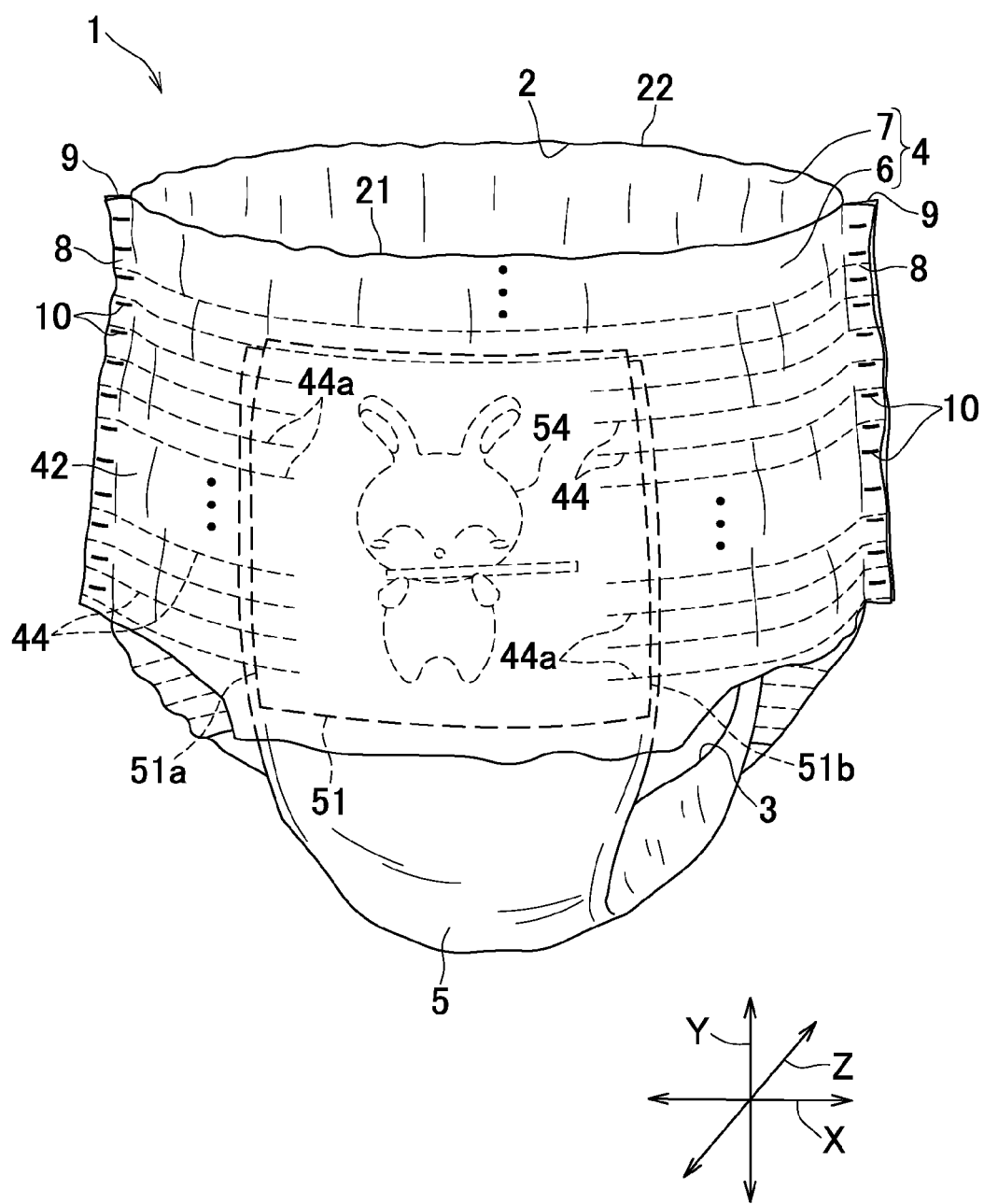
FIG. 1 is a perspective view of a disposable diaper according to a first embodiment of this invention as viewed from the side of a front waist region thereof.
Figure 2:
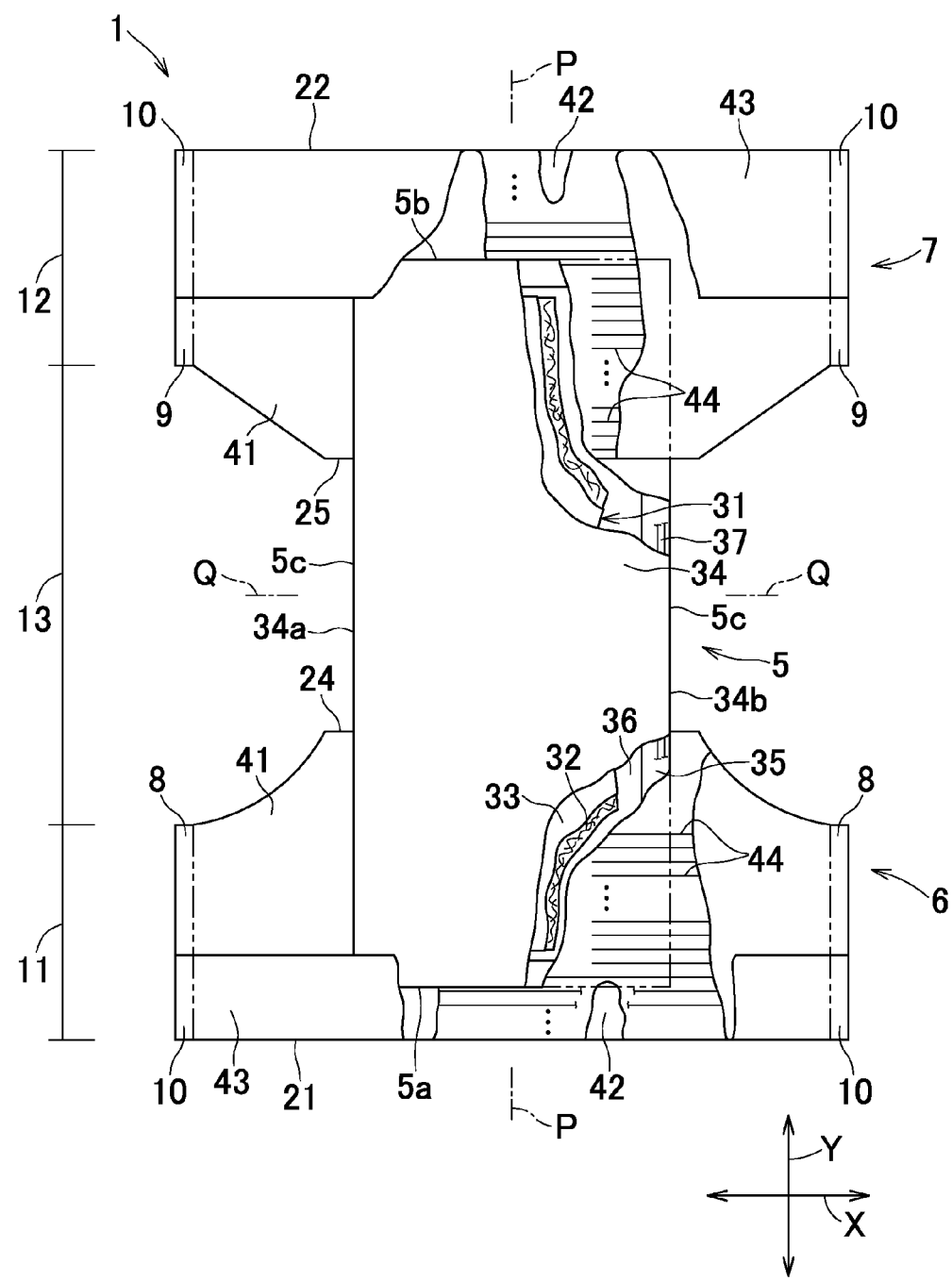
FIG. 2 is a partially cutaway plan view of the diaper flatly developed against contraction after opposite side edges of the diaper have been released from a joined state.

Referring to FIGS. 1 and 2, a diaper 1 is of pull-on type and has a waist-opening 2 and a pair of leg-openings 3. In FIGS. 1 and 2, X indicates a transverse direction, Y indicates a longitudinal direction orthogonal to the transverse direction X and Z indicates a front-back direction orthogonal to both the transverse direction X and the longitudinal direction Y.

The diaper 1 includes an annular waist member 4 extending in a body-cross direction and an intermediate member 5 extending in the longitudinal direction Y.

The waist member 4 includes a front waist member 6 and a rear waist member 7. The diaper 1, more specifically, the annular waist member 4 and the intermediate member 5 respectively have skin-facing sides defining respective inner surfaces thereof and non-skin-facing sides defining respective outer surfaces thereof.

The front and rear waist members 6, 7 respectively have front and rear side edges 8, 9 which are opposite in the transverse direction X and extending in the longitudinal direction Y, respectively. The front and rear side edges 8, 9 have inner surfaces thereof joined together at a pair of series of seams 10 arranged at intervals in the longitudinal direction Y to define the waist-opening 2.

Referring to FIG. 2, P indicates an imaginary longitudinal center line bisecting the diaper 1 in the transverse direction X and Q indicates an imaginary transverse center line bisecting the diaper 1 in the longitudinal direction Y.

The diaper 1 is configured symmetrically about the imaginary longitudinal center line P.

The diaper 1 includes a front waist region 11, a rear waist region 12 and an intermediate region 13 lying between the front and rear waist regions 11, 12 wherein these regions 11, 12, 13 are contiguous to one another in the longitudinal direction Y. The front and rear waist members 6, 7 respectively have a pair of waist outer end portions 21, 22 and a pair of waist inner end portions 24, 25 opposed to each other in the longitudinal direction Y and extending in the transverse direction X, respectively.

The intermediate member 5 is located between the front waist member 6 and the rear waist member 7 in the longitudinal direction Y and coupled to these members 6, 7. Specifically, a front end 5*a* of the intermediate member 5 is joined to the front waist member 6 and a rear end 5*b* of the intermediate member 5 is joined to the rear waist member 7, with the front and rear end portions 5*a*, 5*b* overlapped on the inner surface of the front and rear waist members 6, 7. The front and rear side edges 8, 9 are joined together to define the leg-openings 3 between the inner end portions 24, 25 of the front and rear waist members 6, 7 and opposite side edges 5*c* of the intermediate member 5 (See FIG. 1).

The intermediate member 5 includes a liquid-absorbent structure 31, which includes an absorbent core material assembly 32 formed of, for example, wood fluff pulp and superabsorbent polymer particles, a liquid-absorbent and -dispersant sheet 33 formed of, for example, tissue paper, a liquid pervious inner sheet 34 formed of, for example, a fibrous nonwoven fabric adapted to cover at least the skin-facing side of the liquid-absorbent and -dispersant sheet 33 and an outer sheet 35 formed of, for example, a fibrous nonwoven fabric to cover at least the non-skin-facing side of the liquid-absorbent and -dispersant sheet 33. In addition, a leakage-barrier sheet 36 formed of a breathable plastic film is interposed between the liquid-absorbent and -dispersant sheet 33 and the outer sheet 35. The leakage-barrier sheet 36 may be substantially the same as or larger than the core material assembly 32 in length and width and functions to prevent body exudates absorbed by the core material assembly 32 from leaking to the non-skin-facing side. The front and rear end portions 5*a*, 5*b* of the intermediate member 5 including such liquid-absorbent structure 31 may be covered with folded portions 43 of an outer sheet 42 to be described later to prevent the core material assembly 32 from dropping out of the liquid-absorbent structure 31.

Leg elastics 37 are contractibly attached under tension between the inner sheet 34 and the outer sheet 35 so as to extend in the longitudinal direction Y in parallel to side edges opposed in the transverse direction X of the liquid-absorbent structure 31.

Figure 3:
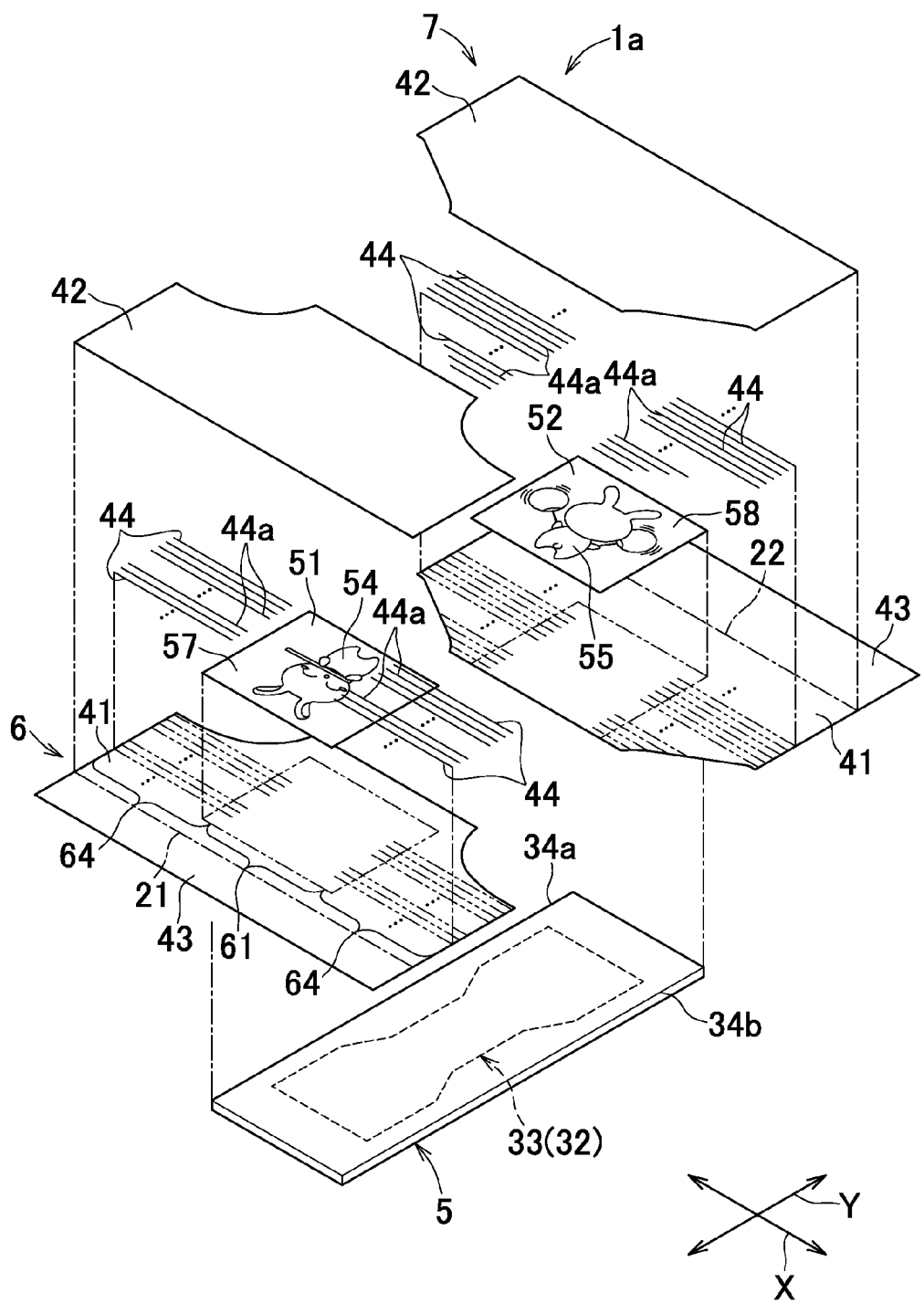
FIG. 3 is an exploded perspective view of the diaper.

The core material assembly 32 has its side edges curved inwardly in the transverse direction X substantially in its middle section in the longitudinal direction Y (See FIG. 3). Such configuration of the core material assembly assures the diaper 1 to fit about the wearer's legs when the diaper 1 is put on the wearer's body. Opposite side edges 34*a*, 34*b* of the inner sheet 34 and the outer sheet 35 extending outwardly beyond opposite sides in the transverse direction X of the core material assembly 32 define respective pairs of side flaps and the leg elastics 37 are attached under tension between the respective side flaps with an adhesive (not shown). With the diaper put on the wearer's body, the side flaps curved or bend upwardly toward the wearer's skin to define a leakage-barrier against the leakage of body exudates. In this regard, leakage-barrier cuffs formed of, for example, a fibrous nonwoven fabric may replace the side flaps or may be formed on the skin-facing side of the intermediate member 5 separately to the side flaps, thereby forming leakage-barriers to prevent the leakage of body exudates.

The front and rear waist members 6, 7 has an inner sheet 41 formed of, for example, a fibrous nonwoven fabric adapted to define the skin-facing side and an outer sheet 42 formed of, for example, a fibrous nonwoven fabric adapted to define the non-skin-facing side. The outer sheet 42 preferably has a light transmission rate of about 75% or higher and more preferably has a light transmission rate of about 83% or higher.

The outer sheet 42 is folded along the waist outer end portions 21, 22 onto the skin-facing side to form folded portions 43. The front and rear end portions 5*a*, 5*b* of the intermediate member 5 are covered with these folded portions 43, respectively.

A plurality of waist elastics 44 extend in the transverse direction X and are attached with adhesives (not shown) distributed between the inner and outer sheets 41, 42. As the waist elastics 44, for example, thread, string or strand materials having the rubber-like elasticity and formed of thermoplastic synthetic resin fibers of such as elastic polyurethane may be used. The waist elastics 44 are arranged, for example, at regular intervals in the longitudinal direction between the crotch end portions 24, 25 and the waist outer end portions 21, 22, respectively.

Referring again to FIG. 2, the waist elastics 44 arranged in a region of the front waist member 6 defined between the waist-opening 2 and the front end 5a of the intermediate region 5 in the longitudinal direction Y continuously extend without defining inelastic regions 61 (see FIG. 3) to be described later which are created by a treatment such as cutting or cutting off as will be described later and continuously extend in the transverse direction X. As these waist elastics 44 in this region, preferably, for example, those having a fineness in a range of about 620 to about 940 dtex are attached under tension at an elongation ratio in a range of about 2.2 to about 2.6 to the inner and outer sheets 41, 42. These waist elastics 44 function to keep the upper portion of the front waist member 6 in contact with the wearer's front waist with a desired fit.

The waist elastics 44 arranged in a region defined between the crotch front end 5a and the front end of the core material assembly 32 continuously extend in the transverse direction X without defining the inelastic regions 61 to be described later which are created by a treatment such as cutting back or cutting off. As these waist elastics 44 used in this region, preferably, for example, those having a fineness in a range of about 470 to 940 dtex are attached under tension at an elongation ratio in a range of about 1.9 to about 2.4 between the inner and outer sheets 41, 42. These waist elastics 44 function to keep the inner sheet 34 and the other sheets in contact with the wearer's front waist with a desired fit.

The waist elastics 44 arranged in a region defined below the front end of the core material assembly 32 define the inelastic region 61 which are created by a treatment such as cutting back or cutting off as will be described later in a midsection in the transverse direction X. As these waist elastics 44, preferably, for example, those having a fineness in a range of about 320 to 780 dtex are contractibly attached under tension at an elongation ratio in a range of about 2.6 to about 3.5 to the inner and outer sheets 41, 42 and to a front graphic sheet 51. These waist elastics 44 overlap the core material assembly 32 and function to put the core material assembly 32 in close contact with the wearer's skin. In order that these waist elastics 44 can put the core material assembly 32 in close contact with the wearer's skin in spite of defining the inelastic region 61, it is desired for these waist elastics 44 to have a sufficient contractile force. From this viewpoint, these waist elastics 44 in this region have an elongation ratio set to be higher than that of the waist elastics 44 in the aforementioned other regions. When the waist elastics 44 are arranged to have such a relatively high elongation ratio, if the number of the waist elastics 44 per unit length in the longitudinal direction Y is relatively small, the waist elastics 44 apt to locally dig into the wearer's skin. To avoid such a situation, by arranging the number of the waist elastics 44 per unit length in the longitudinal direction Y to be relatively large, a plurality of the waist elastics 44 may allow the core material assembly 32 overall come in close contact with the wearer's skin. In this way, it is possible to prevent the individual waist elastics 44 from locally digging into the wearer's skin. In consideration of this, use of the waist elastics 44 having a fineness in a range of about 320 to about 500 dtex in this region is more preferable and arrangement of them at the intervals of 6 mm or less is even more preferable.

The details of the front waist members 6 having been described hereinabove are applicable also to the rear waist members 7.

In this regard, the elongation ratio of the waist elastics 44 may be determined by procedures as follows:

first, the inner and outer sheets 41, 42 are stretched until wrinkles due to the contraction of the waist elastics 44 disappear; then, marks are placed on the waist elastics 44 to indicate a given dimension A in the transverse direction X (the length direction); thereafter, the waist elastics 44 are removed from between the inner and outer sheets 41, 42 and, in this step of removal, the adhesive with which the waist elastics 44 are attached between the inner and outer sheets 41, 42 and the other sheets is solved using solvent such as toluene until the waist elastics 44 become free from any residual of the adhesive; and finally a dimension B in the length direction in the non-stretched state (natural state) is measured and the dimension A is divided by the dimension B to calculate the elongation ratio.

Referring to FIG. 3, in the front and rear waist members 6, 7, substantially rectangular graphic sheets 51, 52 are interposed between the inner sheets 41 and the outer sheets 42, respectively.

As materials for the front and rear graphic sheets 51, 52, thermoplastic synthetic resin films, fibrous nonwoven fabrics or papers may be used.

The front and rear graphic sheets 51, 52 are printed on the non-skin-facing side substantially in respective midsections thereof in the transverse direction X with front and rear graphics 54, 55, respectively, so that these front and rear graphics 54, 55 may be visually recognized through the light transmissive outer sheets 42, respectively. Around the front and rear graphics 54, 55 on the front and rear graphic sheets 51, 52, front and rear graphic-nonexistent regions 57, 58 are defined.

The front graphic sheet 51 on the front waist member 6 is printed with a graphic 54 representing a character's front side and the rear graphic sheet 52 on the rear waist member 7 is printed with a graphic 55 representing the character's rear side. By differentiating the front and rear graphics depending on the front and rear graphic sheets 51, 52 in this manner, it is possible to utilize these graphics as indicators to discriminate the front side and the rear side of the diaper 1, thereby preventing the diaper 1 from being erroneously put on the wearer's body on backwards.

Figure 5:
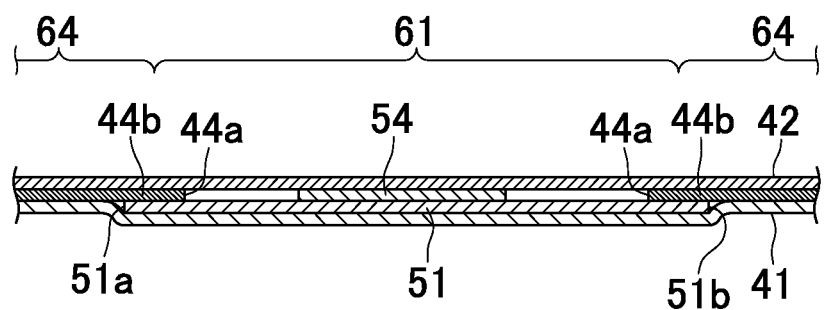
FIG. 5 is a sectional view taken along line V-V in FIG. 4 (*a*).

FIG. 4 (*a*) is a front view of the diaper 1 and FIG. 4 (*b*) is a rear view of the diaper 1. FIG. 5 is a sectional view taken along line V-V in FIG. 4 (*a*).

The waist elastics 44 are cut in respective middle portions in the transverse direction X of the front and rear waist members 6, 7 to define front and rear inelastic regions 61, 62 free from the contractile force of the waist elastics 44. More specifically, the waist elastics 44 in a state stretched in the transverse direction X are cut at the respective middle portions thereof to let the waist elastics 44 contract outward (snapback) in the transverse direction X to define, in the respective middle portions in the transverse direction X of the front and rear waist elastics, the front and rear inelastic regions 61, 62 free from influence of the contractile force of the waist elastics 44. Simultaneously, in opposite laterals of the front and rear waist members, 6, 7, front and rear elastic regions 64, 65 subjected to the contractile force of the waist elastics 44 are defined. In order that the opposite laterals of the waist elastics may contract outward after the respective middle portions thereof have been cut, these middle portions of the waist elastics are previously not joined to any one of the opposite surfaces of the inner and outer sheets 41, 42. In this regard, for operation of cutting the middle portions of the waist elastics 44, heating means or a cutter may be used.

In the front and rear inelastic regions 61, 62, the surface on which the graphics 54, 55 are printed faces the skin-facing side of the outer sheet 42 and free and noncontractile end portions 44a of the waist elastics 44 attached neither to the inner sheet 41 nor to the outer sheet 42 with adhesives lie on opposite side edges 51a, 51b in the transverse direction X of the front and rear graphic sheets 51, 52.

The end portions 44a of the waist elastics 44 have no contractility but the portions 44b other than the end portions 44a have contractility. In this diaper 1, the end portions 44a of the waist elastics 44 having no contractility are interposed between the front and rear graphic sheets 51, 52 and the outer sheet 42 and extend from the outside of the front and rear graphic sheets 51, 52 across the opposite side edges 51a, 51b thereof into the graphic sheets 51, 52. The portions 44b of the waist elastics 44 having contractility also extend from the outside of the front and rear graphic sheets 51, 52 across the opposite side edges 51a, 51b into the graphic sheets 51, 52. The end portions 44a of the waist elastics 44 lie between the opposite side edges 51a, 51b of the front and rear graphic sheets 51, 52 and the front and rear graphics 54, 55.

In such a diaper 1, the noncontractile end portions 44a of the waist elastics 44 lie in the front and rear inelastic regions 61, 62 so as to be interposed between the front and rear graphic sheets 51, 52 and the outer sheet 42 and extend from the outside of the front and rear graphic sheets 51, 52 across the opposite side edges 51a, 51b thereof into the front and rear graphic sheets 51, 52. Such an arrangement allows the end portions 44a of the waist elastics 44 to be visually recognized through the non-skin-facing sides of the respective outer sheets 42. In addition, the end portions 44a of the waist elastics 44 lie between the opposite side edges 51a, 51b of the front and rear graphic sheets 51, 52 and the front and rear graphics 54, 55, respectively. With such an arrangement, it may be clear as a result of visual recognition that if the end portions 44a overlap the front and/or rear graphics 54, 55, this is for the reason that the length of the noncontractile end portions 44a after the snapback is excessive, and if the end portions 44a are spaced from the opposite side edges 51a, 51b of the front and/or rear graphic sheets 51, 52, this is for the reason that the length in the transverse direction X of the waist elastics 44 is insufficient. In each case, it is clearly indicated that the operation of cutting back or cutting away the waist elastics 44 is defective. By utilizing the graphics in this manner, it can be easily recognized with the naked eyes whether the operation of cutting back or cutting away the waist elastics 44 is properly done or not.

The front and rear graphics 54, 55 of the front and rear waist members 6, 7 are allocated in the front and rear inelastic regions 61, 62 and such allocation makes it possible to reduce a possibility that the front and rear graphics 54, 55 might develop wrinkles under the effect of contractile force of the waist elastics 44. Consequently, the front and rear graphics 54, 55 should not be difficult to see.

As illustrated in FIG. 3, the front and rear inelastic regions 61, 62 are allocated so as to overlap the core material assembly 32 (See FIG. 3) so that the portions of the core material assembly 32 overlapping with the front and rear inelastic regions 61, 62 may be also free from the contractile force of the waist elastics 44 and, in consequence, the core material assembly 32 is unlikely to get wrinkled/creased. Consequentially, leakage of body exudates due to the development of wrinkles in the core material assembly 32 may be prevented.

Though not illustrated, on the assumption that the width in the transverse direction X of the core material assembly 32 is substantially the same as the width in the transverse direction X of the front and rear graphic sheets 51, 52, if, in an overlap region of the front and rear graphic sheets 51, 52 and the liquid-absorbent structure 31, the portions 44b having contracting property of the waist elastics 44 is visually recognized to extend across the opposite side edges 51a, 51b of the front and rear graphic sheets 51, 52 and the end portions 44a of the waist elastics 44 is visually recognized, it will be easily confirmed that the elastic regions 64, 65 and the front and rear inelastic regions 61, 62 partially overlap the core material assembly 32 and the core material assembly 32 is put in close contact with the wearer's body under the effect of the waist elastics 44 unless there is any other abnormality.

The front and rear inelastic regions 61, 62 can be easily defined merely by cutting the middle portions of the waist elastics 44 attached under tension.

The waist elastics 44 are cut preferably along a single line extending across the middle portions of the waist elastics 44 so that the portions of the waist elastics 44 joined neither to the inner and outer sheets 41, 42 nor to the front and rear graphic sheets 51, 52 may contract under the contractile force of these portions themselves and remain on distal sides of the portions of the waist elastics 44 joined to the inner and outer sheets 41, 42 and to the front and rear graphic sheets 51, 52 in the form of the end portions 44a having lost their own intrinsic contractile force. If the free portions of the waist elastics 44 are cut along two or more lines extending across these free portions, chips might stay behind in the diaper 1 and the end portions 44a might be misidentified. In contrast, there is no such possibility where the free portions are cut along a single line across the waist elastics 44. Cutting of the waist elastics 44 is carried out preferably in the middle portions thereof joined neither to the inner and outer sheets 41, 42 nor to the front and rear graphic sheets 51, 52. By cutting the waist elastics 44 in this manner, the length in the transverse direction X of the end portions 44a having lost their intrinsic contractile force may be uniformed on both sides. In this regard, however, it is not essential to cut the waist elastics 44 along a single line extending across them and it is also not essential to cut the middle portions joined neither to the inner and outer sheets 41, 42 nor to the front and rear graphic sheets 51, 52.

It is also possible to define the front and rear inelastic regions 61, 62 by cutting off the middle portions of the waist elastics 44 over ranges corresponding to the front and rear inelastic regions 61, 62. In this case also, it is essential that the portions to be cut off are not attached to the opposed surfaces of the inner and outer sheets 41, 42 with an adhesive.

Both the front and rear waist members 6, 7 are formed on the respective midsections in the transverse direction X with the front and rear graphics 54, 55 so that these graphics 54, 55 may be easily recognizable with the naked eyes. In this regard, it is possible to form only one of the front and rear waist members 6, 7 with the graphic 54 or 55.

Though not illustrated, line-drawn portions of the front and rear graphics 54, 55 or these line-drawn portions and portions surrounded by the line-drawn portions may be colored in black, on one hand, and the waist elastics 44 may be colored in white, on the other hand. Brightness of the line-drawn portions and the portions surrounded by the line-drawn portions may be reduced while brightness of the waist elastics 44 may be enhanced to differentiate the brightness of the front and rear graphics 54, 55 and the waist elastics 44 and thereby to improve visibility of the end portions 44a of the waist elastics 44. It should be noted here that it is also possible to differentiate not only the brightness but also to differentiate color phase. For example, it is possible to color the line-drawn portions of the front and rear graphics 54, 55 in yellow and to color the waist elastics 44 in blue so that the front and rear graphics 54, 55 and the waist elastics 44 may be in a complementary color relationship. In this way, the visibility of the end portions 44 can be further improved. Furthermore, it is also possible to replace differentiation of brightness or color phase by differentiation of color saturation. Effective differentiation is not limited to any one of the color phase, the brightness and the color saturation but two or more thereof may be differentiated as the case may be. The front and rear graphics are not limited to the characters but the other elements such as letters, figures and signs may also be used as the graphics. As for the positions of the end portions 44a, an alternative arrangement is also possible such that the end portions 44a of the waist elastics 44 are not interposed between the opposite side edges 51a, 51b of the front and rear graphic sheets 51, 52 and the front and rear graphics 54, 55 but lie on the front and rear graphics 54, 55. With the diaper constructed in this manner, visual recognition of the end portions 44a of the waist elastics 44 is further facilitated.

It is not essential to configure the diaper 1 symmetrically about the imaginary longitudinal center line P. For example, it is possible to cut the waist elastics 44 not in the middle portions thereof but in the portions biased toward the left or the right so that the length in the transverse direction X of the end portions 44a having lost their intrinsic contractility on side may be different from the length in the transverse direction x of the end portions 44a on the other side. With such an arrangement, for example, the end portions 44a of the waist elastics 44 on one side in the transverse direction X may lie on the front and rear graphics 54, 55 and the end portions 44a of the waist elastics 44 on the other side in the transverse direction X lie between the front and rear graphics 54, 55 and the respective opposite side edges 51a, 51b of the front and rear graphic sheets 51, 52 but not on the front and rear graphics 54, 55. In such an embodiment, the end portions 44a on right and left sides in the transverse direction X may be compared to each other to make it further easy to recognize with the naked eyes whether the operation such as cutting was properly carried out or not.

Figure 6:
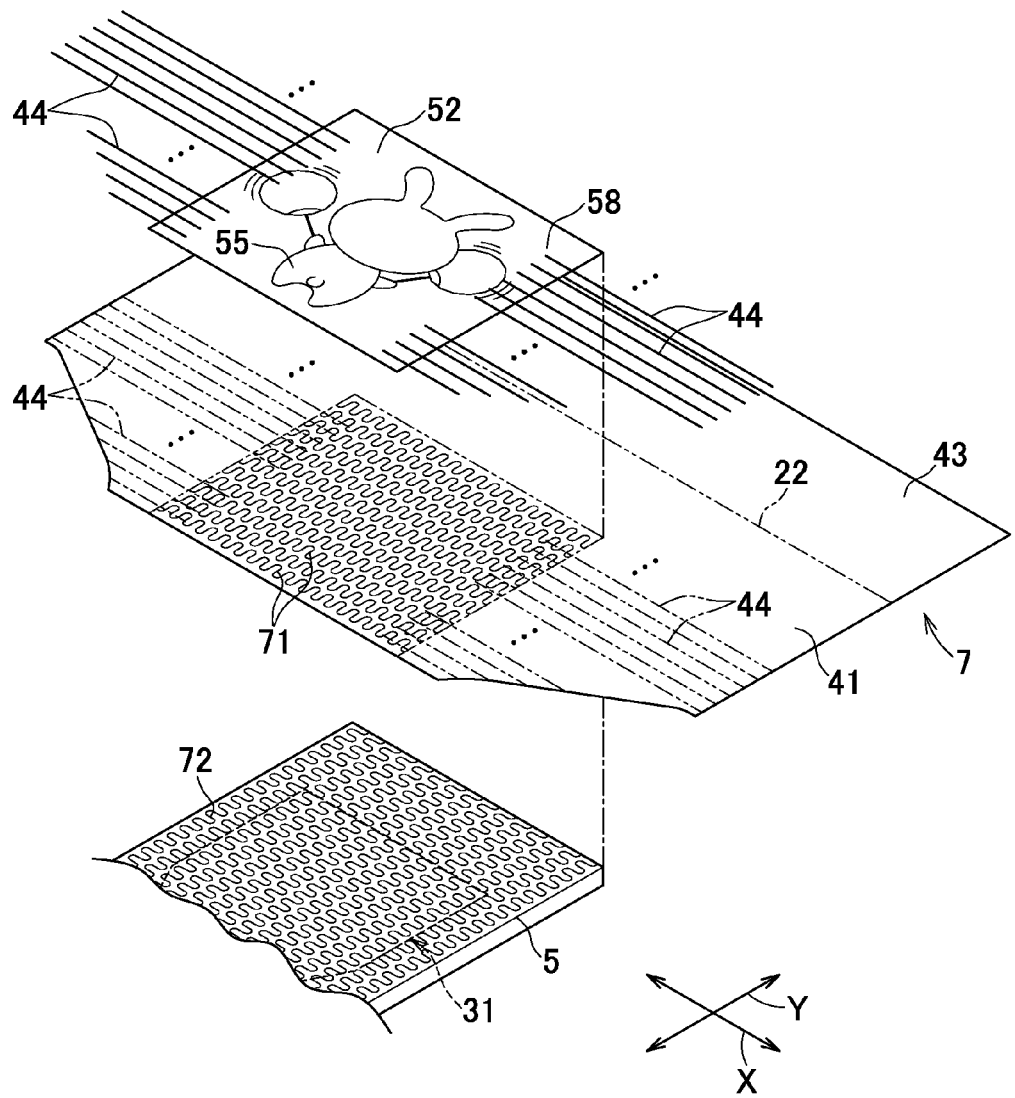
FIG. 6 is a perspective view of a relevant part indicating a direction in which adhesives are distributed.

Additionally, as illustrated in FIG. 6, for example, the inner sheet 41 is distributed with a first hot melt adhesive (first adhesive) 71 in a wavy pattern undulating in the transverse direction X to bond the inner sheet 41 and the rear graphic sheet 52 to each other and the liquid-absorbent structure 31 is distributed with a second hot melt adhesive (second adhesive) 72 in a wave-pattern undulating in the longitudinal direction Y to join the inner sheet 41 and the liquid-absorbent structure 31 to each other. The direction in which the inner sheet 41 is distributed with the first hot melt adhesive 71 with which the inner sheet 41 and the rear graphic sheet 52 are joined to each other and the direction in which the liquid-absorbent structure 31 is distributed with the second hot melt adhesive 72 may be set to intersect with each other in this manner to reduce a possibility that the rear graphic sheet 52 might get wrinkled, thereby facilitating the waist elastics 44 on the rear graphic sheet 52 to be visually recognized. In the transverse direction X, the width of the rear graphic sheet 52 may be fitted to the width of the core material assembly 32 to reduce a possibility that not only the rear graphic sheet 52 but also the core material assembly 32 might get wrinkled, thereby enhancing the absorption efficiency.

It should be noted here that the distributing pattern of the adhesive is not limited to the wave-pattern but the other various patterns such as a Greek capital omega pattern may be adopted. The front graphic sheet 51 also may be joined to the inner sheet 41 similarly to the rear graphic sheet 52.

Second Embodiment

FIG. 7 is a front view illustrating a substantial part of the disposable diaper 100 according to a second embodiment of this invention. This embodiment is similar to the first embodiment in the basic construction and the common constituents are designated by the common signs. These common constituents will not be repetitively described and only the features distinguished from those of the first embodiment will be described hereunder.

On the front graphic sheet 151 of this diaper 100, three graphics 154, 159 are displayed in the transverse direction X. The central graphic 154 is allocated in a midsection in the transverse direction X and the lateral graphics 159 are allocated symmetrically in the transverse direction about the central graphic 154.

As illustrated, the lateral graphics 159 are relatively narrow in the transverse direction X and the central graphic 154 is relatively wide in the transverse direction X.

The end portions 44a having lost their intrinsic contractility of the waist elastics 44 lie on the respective lateral graphics 159.

In the diaper 100 according to this embodiment, the front graphic sheet 151 has at least the central graphic 154 and the lateral graphics 158, 159, the noncontractile end portions 44a of the waist elastics 44 are interposed between the graphic sheet 151 and the outer sheet 42 in the inelastic region 61 so as to lie between the opposite side edges 51a, 51b of the graphic sheet 151 and the central graphic 154. With such an arrangement, the end portions 44a of the waist elastics 44 can be visually recognized from the non-skin-facing side of the outer sheet 42. Consequently, the end portions 44a of the waist elastics 44 may be visually recognized and the graphics may be utilized to check with the naked eyes whether the operation of cutting back or cutting away the waist elastics 44 is properly done or not.

In addition, the presence of the lateral graphics 159 should not bother the wearer by a feeling of strangeness, because, in the transverse direction X, the lateral graphics 159 are relatively narrow and the central graphic 154 is relatively wide.

In this regard, the size differentiation between the central graphic 154 and the lateral graphics 159 is not limited in the transverse direction X but the size of these graphics may be differentiated not only in the transverse direction X but also in the longitudinal direction.

In this diaper 100, line-drawn portions of the lateral graphics 159 or these line-drawn portions and portions surrounded by the line-drawn portions of the lateral graphics 159 may be colored in black. In contrast, the waist elastics 44 may be colored in white to differentiate brightness of the waist elastics 44 and the lateral graphics 159, thereby improving the visibility of the end portions 44a of the waist elastics 44. Additionally, only the line-drawn portion of the central graphic 154 may be colored in black or any other color to alleviate a feeling of strangeness of the front graphic sheet 151.

It should be noted here that it is also possible to differentiate the waist elastics 44 and the lateral graphics 159 not in the brightness but in the color phase or the color saturation. Effective differentiation is not limited to anyone of the color phase, the brightness and the color saturation but two or more thereof may be differentiated as the case may be.

The number of the graphics 154, 158, 159 displayed on the front graphic sheets 151 is not limited to three but four or more may be displayed thereon. It is not essential to display a pair of the lateral graphics 159 on both sides of the central graphic 154, respectively, but it is possible to display the lateral graphic 159 on any one of both sides.

Whole arrangements of the graphics has been described above with respect to the front graphic sheet 151 associated with the front waist member 6, such arrangements are applicable to the rear graphic sheet associated with the rear waist member 7 though not illustrated.

Now a method for measuring a light transmission rate of the outer sheet 42 will be exemplified hereunder.

The light transmission rate may be measured by using, for example, color-difference meter of flicker photometer type Z-300A manufactured by Nippon Denshoku Industries Co., Ltd. in accordance with procedures as follows.

First, a shield is placed between a pair of detector means and measurement is conducted in this condition to make zero point adjustment.

Second, the shield having been placed between the pair of detector means is removed and measurement is conducted in this shield-less condition to make standard adjustment.

Finally, the outer sheet 42 including the front and rear waist elastics 44 as the object to be measured is placed between the pair of detector means and measurement is conducted in this condition.

In some embodiments of the diaper 1 using, for example, an SMS (spunbonded/meltblown/spunbonded) fibrous nonwoven fabric, which is composed by laminating a spunbonded fibrous fabric, a meltblown nonwoven fabric and another spunbonded fibrous nonwoven fabric in this order, a spunbonded fibrous nonwoven fabric and an air-through fibrous nonwoven fabric as materials for the outer sheet 42, the visibility of the waist elastics 44 was determined. The waist elastics 44 of 320 dtex were used and snapped back from the state elongated at a ratio of 3.2.

A first object to be measured was the SMS fibrous nonwoven fabric of 10 g/m$^2$, a second object to be measured was the SMS fibrous nonwoven fabric of 13 g/m$^2$, a third object to be measured was the spunbonded fibrous nonwoven fabric of 17 g/m$^2$, a fourth object to be measured was the air-through fibrous nonwoven fabric of 30 g/m and a fifth object to be measured was the air-through fibrous nonwoven fabric of 60 g/m$^2$.

Measured values of light transmission rates were 87.3% for the first object, 83.2% for the second object, 84.4% for the third object, 73.2% for the fourth subject and 56.8% for the fifth object.

Through the fourth and fifth objects, the end portions 44a of the front and rear waist elastics 44 were less-visible while through the first to third objects, the end portions 44a of the front and rear waist elastics 44 were easily visible. In the result of the similar measurement having been conducted on the other types of fibrous nonwoven fabric, at the light transmission rate lower than 75%, the end portions 44a are less-visible while at the light transmission rate of 75% or higher, the end portions 44a are easily visible. At the light transmission rate of 83% or higher, visual recognition of the end portions 44a becomes further easier.

It should be appreciated that the diapers 1, 100 are not limited to the above-mentioned embodiments but may appropriately modified without departing from the scope of this invention. For example, this invention is not limited to the diapers 1, 100 but applicable also to the toilet-training pants, the incontinent briefs or the like.

While the above-mentioned embodiments have been described on the basis of the pull-on diapers 1, 100, this invention is applicable also to so-called open-type diapers.

In the above-mentioned embodiments, the inner sheet 41 and the outer sheet 42 may be joined to each other with hot melt adhesive distributed to any one of the inner and outer sheets 41, 42 or hot melt adhesive distributed to both the inner and outer sheets 41, 42. In this regard, however, it is not essential to use adhesives such as hot melt adhesives to join the inner and outer sheets 41, 42 to each other but it is also possible, for example, to interpose a heat-sealable sheet between the inner and outer sheets 41, 42 and join each other by heating this heat-sealable sheet. It should be appreciated that the inner and outer sheets 41, 42 may be joined to each other by ultrasonic sealing technique without heating.

It is also not essential that the inner and outer sheets 41, 42 are respectively divided into those in the front waist member 6 and the rear waist member 7 but the inner and outer sheets 41, 42 may be prepared in the form of the sheets continuous from the front waist region 11 to the rear waist region 12, respectively.

Specific numeric values such as the elongation ratios of the waist elastics 44 are not limited to them as have been described above but may appropriately varied.

It is also possible to form the front and rear graphic sheets 51, 52, 151 on the non-skin-facing side thereof with concavities which are concave from the non-skin-facing side toward the skin-facing side.

In one example of the method for forming such concavities, a surface treating device including a discharging electrode and a dielectric covered roll having a plurality of convexities on a peripheral surface thereof is used so that the desired treatment may be achieved by repeating pulse corona discharge. Specifically, the discharge electrode and the dielectric covered roll are set up to face each other with a predetermined distance therebetween. Keeping the graphic sheet in close contact with the roll and keeping an air gap between the lower surface of the graphic sheet and the discharge electrode, the graphic sheet is guided through this air gap. A local dielectric breakdown occurs between the discharge electrode and the convexities on the roll to initiate discharge from the discharge electrode toward the convexities on the roll. Thereupon, electric current discharged toward the convexities forms the graphic sheets 51, 52, 151 with convexities/debosses.

By forming the graphic sheets 51, 52, 151 with the convexities/debosses, the bonding effect between the inner and outer sheets 41, 42 and the graphic sheets 51, 52, 151 with hot melt adhesive or other techniques may be enhanced.

The component elements of the diapers 1, 100 are not limited to those described in this specification but the other various types of material widely used in the relevant technical field may be used without limitation unless otherwise stated.

The terms "first" and "second" used in the description and claims of this invention are used merely to distinguish the similar elements, similar positions or the other similar means.

REFERENCE SIGNS LIST

1 diaper
31 liquid-absorbent structure
41 inner sheet
42 outer sheet
44 waist elastics
44a end portions
51 front graphic sheet (graphic sheet)
52 rear graphic sheet (graphic sheet)
54 front graphic (graphic)
55 rear graphic (graphic)
51a opposite side edges
52a opposite side edges
71 first hot melt adhesive (first adhesive)
72 second hot melt adhesive (second adhesive)
151 graphic sheet

154 central graphic
159 lateral graphics
X transverse direction

The invention claimed is:

1. A disposable diaper having a skin-facing side and a non-skin-facing side, comprising:
   an inner sheet lying on the skin-facing side and an outer sheet lying on the non-skin-facing side each defining the front and rear waist members;
   waist elastics interposed between the inner and outer sheets and extending under a potential contractility in a transverse direction of the front and rear waist members;
   inelastic regions in which none of the waist elastics is present; and
   graphic sheets having graphics adapted to be visually recognized through the outer sheet, wherein:
   respective end portions of the waist elastics interposed between the graphic sheets and the outer sheet extend from the outside of the graphic sheets across opposite side edges of the respective graphic sheets into the respective graphic sheets;
   the end portions of the waist elastics lie on the respective graphics;
   the diaper further includes a liquid-absorbent structure; and
   a distribution direction of a first adhesive with which the inner sheet is joined to the respective graphic sheets intersects with a distribution direction of a second adhesive with which the inner sheet is joined to the liquid-absorbent structure.

2. The diaper defined by claim 1, wherein:
   the end portions of the waist elastics have no contractility and the remaining portions thereof have contractility; and
   the portions of the waist elastics having contractility extend from the outside of the respective graphic sheets across the opposite side edges thereof into the respective graphic sheets.

3. The diaper defined by claim 2, wherein the end portions of the waist elastics lie on the respective graphics.

4. The diaper defined by claim 3, wherein the respective graphics are different from the waist elastics in at least one of color phase, color saturation and brightness.

5. The diaper defined by claim 2, wherein the end portions of the waist elastics lie between the opposite side edges of the respective graphic sheets and the respective graphics.

6. The diaper defined by claim 2, wherein the respective graphics are different from the waist elastics in at least one of color phase, color saturation and brightness.

7. The diaper defined by claim 2, wherein the respective graphics are partially low in brightness and the waist elastics are relatively high in brightness.

8. The diaper defined by claim 1, wherein the end portions of the waist elastics lie between the opposite side edges of the respective graphic sheets and the respective graphics.

9. The diaper defined by claim 8, wherein the respective graphics are different from the waist elastics in at least one of color phase, color saturation and brightness.

10. The diaper defined by claim 1, wherein:
    the respective graphic sheets include at least central graphics and lateral graphics arranged on both sides of the central graphics; and
    the end portions of the waist elastics lie between the opposite side edges of the respective graphic sheets and the respective central graphics.

11. The diaper defined by claim 10, wherein the respective graphics are different from the waist elastics in at least one of color phase, color saturation and brightness.

12. The diaper defined by claim 10, wherein the noncontractile end portions of the waist elastics lie on the respective lateral graphics.

13. The diaper defined by claim 12, wherein the respective graphics are different from the waist elastics in at least one of color phase, color saturation and brightness.

14. The diaper defined by claim 1, wherein the respective graphics are different from the waist elastics in at least one of color phase, color saturation and brightness.

15. The diaper defined by claim 1, wherein the respective graphics are partially low in brightness and the waist elastics are relatively high in brightness.

16. The diaper defined by claim 1, wherein:
    the diaper further includes the liquid-absorbent structure containing therein a core material assembly; and
    in the transverse direction, a width dimension of the core material assembly is substantially the same as a width dimension of each of the graphic sheets.

17. The diaper defined by claim 16, wherein the respective graphics are different from the waist elastics in at least one of color phase, color saturation and brightness.

* * * * *